United States Patent [19]
Alessi

[11] Patent Number: 5,318,021
[45] Date of Patent: Jun. 7, 1994

[54] ENDOTRACHEAL TUBE WITH AUTOMATIC CUFF INFLATION AND DEFLATION

[76] Inventor: David M. Alessi, 555 South Norton Ave., Los Angeles, Calif. 90020

[21] Appl. No.: 710,695

[22] Filed: Jun. 5, 1991

[51] Int. Cl.$^5$ .............................................. A61M 16/00
[52] U.S. Cl. .............................. 128/207.15; 128/207.14
[58] Field of Search ........................ 128/207.14, 207.15; 604/96, 103, 104

[56] References Cited

U.S. PATENT DOCUMENTS

| | | | |
|---|---|---|---|
| 3,481,339 | 12/1969 | Puig | 128/207.15 |
| 3,504,676 | 4/1970 | Lomholt | 128/207.15 |
| 3,565,079 | 2/1971 | Jackson | 128/207.15 |
| 3,616,799 | 11/1971 | Sparks | 128/207.15 |
| 3,707,151 | 12/1972 | Jackson | 128/207.15 |
| 3,709,227 | 1/1973 | Hayward | 128/207.15 |
| 3,734,094 | 5/1973 | Calinog | 128/207.15 |
| 3,769,983 | 11/1973 | Merav | 128/207.15 |
| 4,979,505 | 12/1990 | Cox | 128/207.15 |

Primary Examiner—Edgar S. Burr
Assistant Examiner—Aaron J. Lewis
Attorney, Agent, or Firm—Pretty, Schroeder, Brueggemann & Clark

[57] ABSTRACT

An endotracheal tube adapted for ventilating a patient and provided with an inflatable cuff to force air into the patient's lungs includes at least one port that communicates with the inflatable cuff such that, when air is forced down the tube during ventilation, a portion of the air is forced into the inflatable cuff and inflates it, occluding the trachea. During exhalation, the cuff is allowed to partially deflate. The partial deflation during every breathing cycle improves the blood flow to the tracheal tissues and reduces tissue damage from prolonged intubation.

14 Claims, 1 Drawing Sheet

ENDOTRACHEAL TUBE WITH AUTOMATIC CUFF INFLATION AND DEFLATION

BACKGROUND OF THE INVENTION

1. Field of the Invention

This invention relates to respiratory devices and, more particularly, to endotracheal tubes that are adapted to be inserted down a patient's trachea and to provide air to a patient's lungs.

2. Description of the Related Art

Endotracheal tubes are used to ventilate a patient by forcing air into the patient's lungs. Exhalation naturally follows. Ventilation is necessary, for example, during surgery, after lung failure, or to assist anyone who is having difficulty breathing. An endotracheal tube is an elongated tube that is inserted into the patient's throat and down into the patient's trachea, or windpipe. For easier insertion and reduced chances of tissue damage, the diameter of the tube is somewhat less than the natural diameter of a typical throat. The length of the endotracheal tube is such that the proximal end of the tube is located in the patient's mouth and can be connected to an air supply or breathing apparatus, while the distal end of the tube is located in the patient's trachea, past the vocal cords. During ventilation, air is forced into the open proximal end, down the tube, out the open distal end, and into the patient's lungs. During exhalation, air is allowed to leave the patient's lungs and travel back up the tube.

For effective ventilation, the air forced down the endotracheal tube must enter the lungs with minimal loss of escaping air. Therefore, the air must be blocked from escaping around the open distal end of the tube and flowing back up the patient's trachea in the space between the endotracheal tube and the trachea. Because of the need to block the air, an endotracheal tube is provided with an inflatable cuff that is usually located near the tube's distal end, past the vocal cords. When the distal end of the tube is being inserted down into the patient's trachea, the cuff is maintained in a deflated condition, for easier passage. Thereafter, he cuff is inflated until it presses against, and occludes, the trachea, to prevent the air that leaves the open distal end of the tube from flowing back up the trachea. Rather, the air is forced out the tube's open end, down the remainder of the trachea, and into the patient's lungs. A separate inflation tube that communicates with the cuff is provided along the length of the endotracheal tube. Inflation and deflation of the cuff is controlled by an air valve at the proximal end of the inflation tube.

A serious drawback to using endotracheal tubes is that the inflated cuff causes damage to the soft tissues of the trachea. The tissue damage is believed to be at least partially a result of a reduced blood flow to the soft tissues that follows from inflation of the cuff. Scar tissue can form in the trachea past the vocal cords, which is a condition known as subglottic stenosis. This is a very difficult problem to treat and can require the placement of a tracheostomy tube in the patient, often for the remainder of the patient's lifetime. Unfortunately, ventilation with the endotracheal tube requires the cuff to be inflated.

Studies have indicated that even relatively short periods of cuff inflation can cause damage to the soft tissues. As a result, a patient cannot physically tolerate intubation with an inflated cuff for extensive periods of time, and damage can occur after intubation during relatively short surgeries. Patients often have improved resistance to tissue damage if the cuff is periodically deflated during extended periods of intubation, but under many circumstances, such as surgery, periodic deflation might not be possible. At the very least, it is very inconvenient to constantly inflate and deflate the cuff when using the endotracheal tube, and the tube is often used under circumstances where having to keep track of inflation and deflation is impractical.

From the discussion above, it should be apparent that there is a need for a respiratory device that can be used to ventilate a patient for extended periods of time, without causing damage to the soft tissues of the trachea. The present invention satisfies this need.

SUMMARY OF THE INVENTION

The present invention is embodied in a patient-ventilating endotracheal tube that has an inflatable cuff that is automatically inflated during ventilation and is automatically deflated during exhalation. In a further aspect of the invention, the same air that is forced down the tube into the patient's lungs is used to inflate the cuff. The automatic cuff deflation improves the blood flow to the soft tissues and reduces the soft tissue damage when compared with conventional endotracheal tubes. Because the inflation and deflation occur automatically with every cycle of ventilation and exhalation, there is no need to periodically stop ventilating and deflate the cuff to reduce tissue damage. As a result, the tube can be used for longer uninterrupted periods of time without damaging the tissues. Using the same air to ventilate the patient and inflate the cuff also eliminates the need for a separate cuff inflation tube and air valve.

The endotracheal tube can advantageously use the same air to ventilate the patient and inflate the cuff by means of airholes, or ports, in the tube that communicate with the cuff. The ports, for example, can pass straight through the wall of the tube where the cuff is located. The ports can inflate the cuff because the cuff's resistance to inflation is relatively low and, initially, the resistance of the lungs to ventilation can be quite high. Therefore, the air initially forced down the endotracheal tube will not enter the lungs but will first pass through the ports and into the cuff. After the cuff is inflated, the resistance of the cuff to ventilation is higher than that of the lungs. Therefore, no more air can enter the cuff and the air forced into the tube continues down to the open distal end, where it enters the lungs. The amount of air necessary to inflate the cuff is relatively small, and therefore the efficiency of ventilation does not appreciably suffer by sharing the air in this way.

When the patient is allowed to exhale, the air pressure in the endotracheal tube is reduced below what is required for ventilation, or is even changed to a vacuum, and therefore air can flow out of the cuff, partially deflating it. This relaxes the pressure against the soft tissues, and allows a sufficient blood flow to the tissues to reduce the chance of damage to them. As a result, intubation can be prolonged.

Other features and advantages of the present invention should be apparent from the following description of the preferred embodiment, taken in conjunction with the accompanying drawings, which illustrate, by way of example, the principles of the invention.

DESCRIPTION OF THE PREFERRED EMBODIMENT

Figure 1:
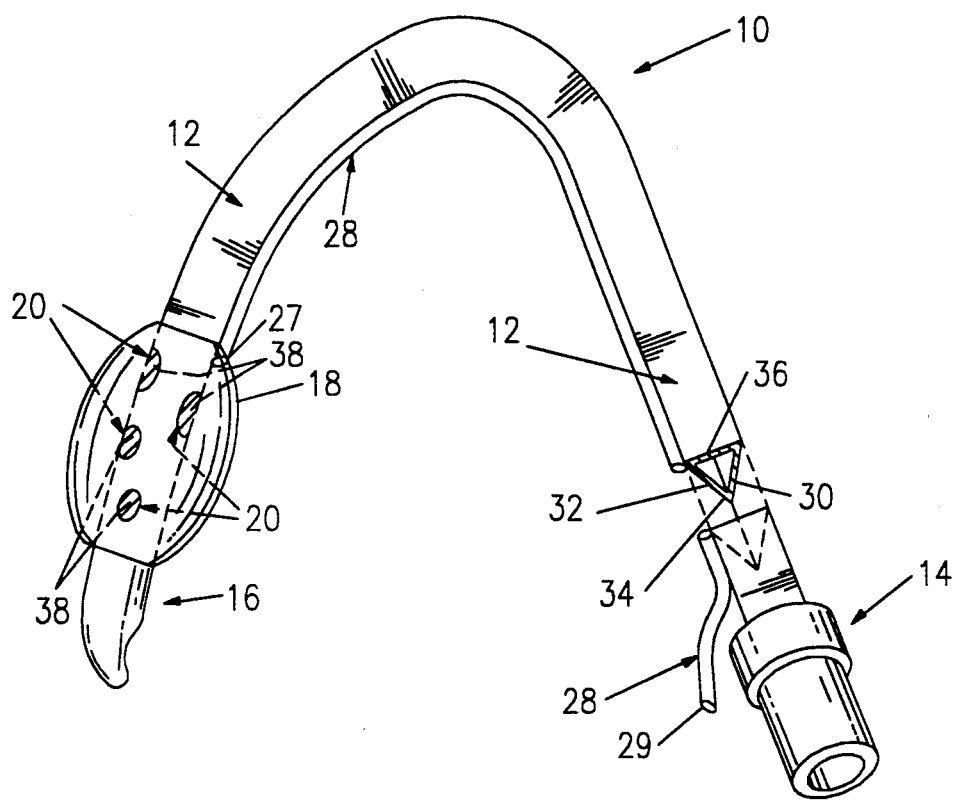
FIG. 1 is a perspective view of an endotracheal tube in accordance with the present invention.

Referring to FIG. 1, an endotracheal tube device 10 in accordance with the present invention comprises a thin-walled, elongated tube 12 having an open proximal end 14 and an open distal end 16. The endotracheal tube includes an inflatable cuff 18 located near the distal end. The tube is sufficiently long so that, when the tube is inserted into a patient's trachea, the distal end and inflatable cuff are located below the patient's vocal cords and the proximal end is located in the patient's mouth. During ventilation of the patient, the cuff is automatically inflated by the air forced down the tube until it is pressed against the soft tissues of the trachea, occluding the trachea and preventing the air that leaves the distal end from proceeding back up the trachea past the cuff. During exhalation, the cuff is automatically deflated sufficiently to allow an improved blood flow to the soft tissues, which reduces the likelihood that the soft tissues will become damaged during extended periods of intubation. The automatic inflation and deflation of the cuff 18 with every ventilation cycle reduces the risk of a subglottic stenosis and makes prolonged intubation more viable.

Figure 2:
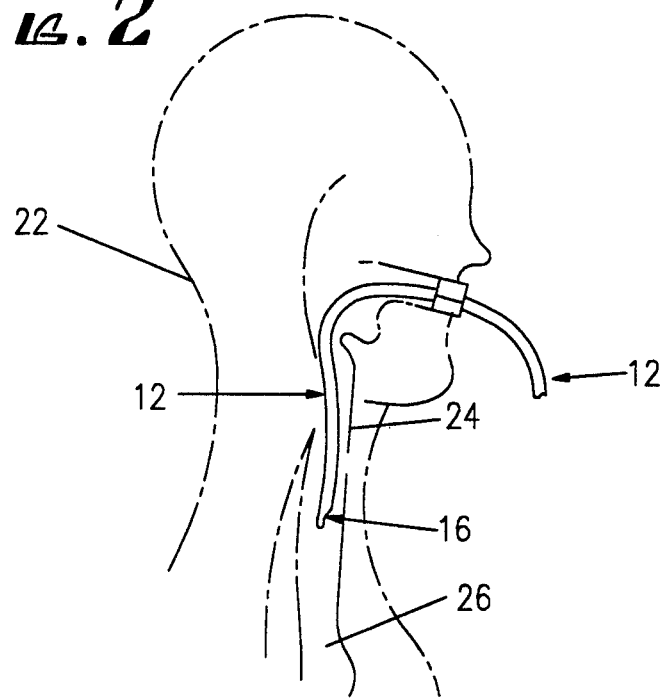
FIG. 2 is a partially cross-section, partially schematic view of the endotracheal tube illustrated in FIG. 1 as inserted in a patient.

In the preferred embodiment, the inflatable cuff 18 is inflated by means of ports 20 in the elongated tube 12 that communicate with the cuff. The ports pass straight through the wall of the elongated tube and utilize the lungs' initial resistance to ventilation. Referring to FIG. 2, when the endotracheal tube 10 is placed in a patient 22 so as to extend down the trachea 24, the annular space between the tube and trachea is sufficiently small and taken up by the collapsed cuff that air will not escape from the distal end and return up the annular space. Rather, because the lungs initially resist ventilation, most of the air forced down the elongated tube will first pass through the ports 20 and into the cuff 18, inflating it. After the cuff is inflated, no more air can enter the cuff and the air forced down the elongated tube 12 will continue out the open distal end 16 and will enter the lungs 26. Because the internal volume of the cuff is relatively small, the amount of air necessary to inflate the cuff is minimal and therefore the efficiency of ventilation does not appreciably suffer by using the same air to inflate the cuff and ventilate the patient.

During ventilation, the proximal end 14 of the endotracheal tube device 10 is connected to an air supply or breathing apparatus (not illustrated). During exhalation, the air pressure in the elongated tube 12 is not as high as it is during ventilation and can even be changed to a vacuum. Therefore, air can flow out of the patient's lungs and back up the tube. Simultaneously, air can flow out of the now-inflated cuff 18 through the ports 20 and back up the tube with the exhaled air from the patient's lungs. In this way, the cuff 18 is at least partially deflated every time the patient is allowed to exhale. The automatic deflation of the cuff relaxes the pressure of the inflated cuff against the soft tissues of the patient's trachea and allows a sufficient blood flow to the soft tissues such that the chance of tissue damage from intubation is greatly reduced. As a result, the patient can tolerate longer periods of intubation. A separate small tube 28 can be used to suck anesthesia gases out of the cuff 18 or to keep the ports 20 clear by blowing air into the cuff. The small tube 28 is attached to the elongated tube 12 and is in flow communication with the cuff at one end 27 and is connected to either an air supply or vacuum line (not illustrated) at the other end 29.

The elongated tube 12 can be constructed from a variety of thin-walled materials, as known to those skilled in the art. The cuff 18 and tube 12 can be of different materials. The distal tip 16 of the tube can be of a different material compared with the rest of the tube, or can be covered with a soft sponge material, to prevent rubbing and abrasion of the trachea 24. All or part of the tube can be provided with metal foil or can be electroplated so it can be used with laser surgery on the larynx. The tube 12 has a uniform outer diameter somewhat smaller than a typical patient's trachea.

The entire elongated tube 12 can be of round or virtually any other cross-sectional shape, so long as the shape is compatible with the patient's trachea. However, in the preferred embodiment shown in FIG. 1, an intermediate portion of the tube 12 between the cuff 18 and the proximal end 14 has a cross-section defined by two substantially straight sides 30 and 32 that converge to a tip 34, with a third side 36 that extends between the two substantially straight sides and curves outwardly away from the tip 34. This shape more closely conforms to the natural shape of the vocal cords and minimizes the force of contact by the elongated tube 12 with the vocal cords, therefore minimizing injury to the vocal cords and the arytenoid cartilage. This cross-sectional shape is described in U.S. patent application Ser. No. 07/315,136 by the present inventor and is incorporated herein by this reference. The proximal end 14 of the tube is provided with a circular cross-section, to better enable connection to the air supply or breathing apparatus.

The ports 20 can be provided with filters 38, such as a sponge-like material, that allow air to pass freely but that substantially prevent patient secretions from passing through. Also, the ports can be round, oval, elongated, or any other shape that allows air to flow freely but that limits the ingress of secretions to a minimum.

The present invention has been described above in terms of the presently preferred embodiment so that an understanding of the present invention can be conveyed. There are, however, many configurations for endotracheal tubes not specifically described herein, but with which the present invention is applicable. The present invention should therefore not be seen as limited to the particular embodiment described herein, but rather, it should be understood that the present invention has applicability with respect to a variety of endotracheal tubes. All modifications, variations, or equivalent arrangements that are within the scope of the attached claims should therefore be considered to be within the scope of the invention.

I claim:

1. An endotracheal tube adapted for ventilating a patient by forcing air down the patient's trachea during a ventilation cycle and allowing air to escape from the patient's lungs during an exhalation cycle, the endotracheal tube having a proximal end with an opening the projects into the patient's oral cavity, having a distal end with an opening that projects into the patient's trachea past the patient's vocal cords, and having an inflatable cuff located near the distal end such that, when the cuff is inflated, the cuff occludes the trachea and prevents air from escaping past the tube's distal end and up the patient's trachea past the vocal cords to the oral cavity, wherein:

the endotracheal tube includes at least one port, distinct from the opening at the tube's distal end, that communicated with the inflatable cuff such that the cuff is automatically inflated via the port and maintained in an inflated condition during the ventilation cycle by the air that is forced down the endotracheal tube during the ventilation cycle and such that the cuff is automatically partially deflated via the port and maintained in a partially deflated condition during the exhalation cycle, and wherein the port is configured to allow air flow sufficient to deflate the cuff to substantially eliminate pressure by the cuff against the trachea during the exhalation cycle.

2. An endotracheal tube as in claim 1, wherein the port comprises an opening having a fixed aperture.

3. An endotracheal tube as in claim 2, wherein the port is configured in a substantially oval shape.

4. An endotracheal tube as in claim 2, wherein the port is configured in a substantially circular shape.

5. An endotracheal tube for use in ventilating a patient by forcing air down the tube and into the patient's lungs, and allowing the patient to exhale by allowing air to leave the patient's lungs, the endotracheal tube having a proximal end with an opening that extends into the patient's oral cavity, having a distal end with an opening that extends into the patient's trachea past the patient's vocal cords, and having an inflatable cuff located near the distal end such that, when the cuff is inflated, the cuff occludes the trachea and prevents air from escaping past the tube's distal end and up the patient's trachea past the vocal cords to the oral cavity, wherein:

the endotracheal tube includes at least one port, distinct from the opening at the tube's distal end, that communicates with the inflatable cuff such that, while the patient is being ventilated and air is forced down the endotracheal tube, a portion of the forced air passes through the port to inflate the inflatable cuff and occlude the trachea, and while the patient is allowed to exhale, a portion of the inflated air in the cuff is allowed to escape through the port into the tube and partially deflate the cuff, and wherein the port is configured to allow sufficient air escape from the cuff during exhalation to deflate the cuff, and to maintain the cuff in a partially deflated condition, thereby reducing the occlusion of the trachea by the cuff.

6. An endotracheal tube as in claim 5, wherein the port comprises an opening having a fixed aperture.

7. An endotracheal tube as in claim 6, wherein the port is configured in a substantially oval shape.

8. An endotracheal tube as in claim 6, wherein the port is configured in a substantially circular shape.

9. An endotracheal tube adapted to be placed in a patient's trachea and used in a ventilation cycle during which the patient is ventilated by forcing air down the tube into the patient' lungs and used in an exhalation cycle during which the patient is allowed to exhale by letting air escape from the lungs back up the tube, the endotracheal tube comprising:

a thin-walled elongated tube having a proximal end and a distal end;

a inflatable cuff located near the distal end such that, when the cuff is inflated, the cuff occludes the trachea and prevents air from escaping past the tube's open end and up the patient's trachea past the vocal cords to the oral cavity; and inflation means including at least one port in the elongated tube, which communicates with the cuff, for directing the air that is forced down the elongated tube during the ventilation cycle into the cuff via the port to maintain the cuff inflated and for allowing the air to escape from the cuff via the port back up the tube during the exhalation cycle to maintain the cuff partially deflated, wherein the inflation means includes at least one port configured to allow air to escape from the cuff during the exhalation cycle, to substantially eliminate the occlusion of the trachea created by the inflated cuff during inhalation.

10. An endotracheal tube as defined in claim 9, wherein the endotracheal tube further includes a small diameter tube that is attached to the elongated tube and that communicates with the inflatable cuff at the small diameter tube's distal end.

11. An endotracheal tube as in claim 9, wherein the port comprises an opening having a fixed aperture.

12. An endotracheal tube as in claim 11, wherein the port is configured in a substantially oval shape.

13. An endotracheal tube as in claim 11, wherein the port is configured in a substantially circular shape.

14. An endotracheal tube adapted to be placed in a patient's trachea and used in a ventilation cycle during which the patient is ventilated by forcing air down the tube into the patient's lungs and used in an exhalation cycle during which the patient is allowed to exhale by letting air escape from the lungs back up the tube, the endotracheal tube comprising:

a thin-walled elongated tube having a proximal end and a distal end;

an inflatable cuff located near the distal end such that, when the cuff is inflated, the cuff occludes the trachea and prevents air from escaping past the tube's open end and up the patient's trachea past the vocal cords to the oral cavity; and inflation means including at least one port in the elongated tube, which communicates with the cuff, for directing the air that is forced down the elongated tube during the ventilation cycle into the cuff via the port to maintain the cuff inflated and for allowing the air to escape from the cuff via the port back up the tube during the exhalation cycle to maintain the cuff partially deflated, wherein the port includes filter means for allowing air to pass freely and substantially preventing the passage of patient secretions.

* * * * *